(12) United States Patent
Kinnon Dahlgren et al.

(10) Patent No.: US 10,548,565 B2
(45) Date of Patent: Feb. 4, 2020

(54) MANUAL, PORTABLE ULTRASONOGRAPHY DEVICE, WITH CENTRALIZED CONTROL AND PROCESSING IN THE HARDWARE AND WITH DISPLAY OUTPUTS, WHICH OPERATES IN REAL TIME WITH A HIGH IMAGE REFRESH RATE

(71) Applicants: UNIVERSIDAD DE CHILE, Santiago (CL); MEGASALUD, Santiago (CL); MAC KINNON Y ASOCIADOS, La Reina-Santiago (CL)

(72) Inventors: John Mac Kinnon Dahlgren, La Reina-Santiago (CL); Manuel Armando Duarte-Mermoud, Santiago (CL); Carlos Eugenio Conca Rosende, Santiago (CL); Nicolás Humberto Beltrán Maturana, Santiago (CL); Rodrigo Andrés Maureira Tenorio, Santiago (CL); Vader Johnson Vera, Santiago (CL); Javier Eduardo Moya Fuentes, Santiago (CL)

(73) Assignees: UNIVERSIDAD DE CHILE, Santiago (CL); MEGASALUD, Santiago (CL); MAC KINNON Y ASOCIADOS, Santiago (CL)

( * ) Notice: Subject to any disclaimer, the term of this patent is extended or adjusted under 35 U.S.C. 154(b) by 1154 days.

(21) Appl. No.: 14/783,028

(22) PCT Filed: Mar. 10, 2014

(86) PCT No.: PCT/CL2014/000008
§ 371 (c)(1),
(2) Date: Oct. 7, 2015

(87) PCT Pub. No.: WO2014/166007
PCT Pub. Date: Oct. 16, 2014

(65) Prior Publication Data
US 2016/0317123 A1    Nov. 3, 2016

(30) Foreign Application Priority Data

Apr. 8, 2013   (CL) .................................. 947-2013

(51) Int. Cl.
*A61B 8/00*     (2006.01)
*G01S 7/52*     (2006.01)
(Continued)

(52) U.S. Cl.
CPC .............. *A61B 8/4427* (2013.01); *A61B 8/08* (2013.01); *A61B 8/14* (2013.01); *A61B 8/462* (2013.01);
(Continued)

(58) Field of Classification Search
CPC ....... A61B 8/4427; A61B 8/56; A61B 8/5207; A61B 8/462; A61B 8/14; A61B 8/54; A61B 8/08; G01S 7/5202; G01S 7/52085
See application file for complete search history.

(56) References Cited

U.S. PATENT DOCUMENTS 6,383,139 B1    5/2002   Hwang et al.
2003/0158482 A1 *  8/2003   Poland ..................... G01H 1/00
                                                    600/446
(Continued)

FOREIGN PATENT DOCUMENTS

EP          1118875 A2      7/2001
EP          1214909 A1      6/2005
WO     WO 2008/146207 A2   12/2008

OTHER PUBLICATIONS

Resolution of Notification of the Expert Response (new Law), Type/Application No. Invention Patent/2013-000947, Santiago, Aug. 2, 2016.
(Continued)

*Primary Examiner* — Peter Luong
(74) *Attorney, Agent, or Firm* — Gottlieb, Rackman & Reisman, P.C.

(57) ABSTRACT

The invention is directed to a handheld portable ultrasound device comprising a transducer further comprising piezo-
(Continued)

electric elements that emit ultrasonic waves and capture echoes from tissues inside of a patient; a processing unit Field Programmable Gate Array comprising a General Control Device module, a Pulse Emission Control module, a Wave Conformation module, and an Image Processing module; Pulse Generation and Front-End Unit having a pulse generator, a plurality of switches transmission/reception, and a Front-End circuit generating digitized signals; an Imaging and Transmission Unit; and a Visualization Device. The General Control Device module coordinates operations of the Pulse Emission Control modules of Beamforming and Image Processing; the Pulse Emission Control module drives the Pulse Generator; the Beamforming module receives digitized signals or samples stream from the Front-End Circuit delivers a coherent summation of digitized signals by applying selective delays to digitized signals. The Image Processing module generates an ultrasound image.

19 Claims, 6 Drawing Sheets

(51) Int. Cl.
*A61B 8/08* (2006.01)
*A61B 8/14* (2006.01)

(52) U.S. Cl.
CPC .............. *A61B 8/5207* (2013.01); *A61B 8/54* (2013.01); *A61B 8/56* (2013.01); *G01S 7/5202* (2013.01); *G01S 7/52085* (2013.01)

(56) References Cited

U.S. PATENT DOCUMENTS

| 2005/0228281 | A1 | 10/2005 | Nefos | |
| 2006/0241490 | A1* | 10/2006 | Lazenby | A61B 8/4483 |
| | | | | 600/472 |
| 2009/0177088 | A1 | 7/2009 | Hasegawa et al. | |
| 2014/0243614 | A1* | 8/2014 | Rothberg | A61B 8/13 |
| | | | | 600/301 |

OTHER PUBLICATIONS

PCT International Search Report for PCT/CL2014/000008, dated Jun. 16, 2014, 3 pages.

English translation of PCT International Search Report for PCT/CL2014/000008, dated Jun. 16, 2014, 3 pages.

* cited by examiner

MANUAL, PORTABLE ULTRASONOGRAPHY DEVICE, WITH CENTRALIZED CONTROL AND PROCESSING IN THE HARDWARE AND WITH DISPLAY OUTPUTS, WHICH OPERATES IN REAL TIME WITH A HIGH IMAGE REFRESH RATE

APPLICATION FIELD

This invention relates to a low cost, portable ultrasound device, with head mounted display. It relates specifically to a portable handheld ultrasound device with control and processing performed completely by using dedicated hardware embedded in a FPGA (Field Programmable Gate Array) processing unit with high resolution display outputs and high frame rate.

DESCRIPTION OF THE PRIOR ART

Generally, traditional ultrasound devices are not restricted in size, energy or processing capacity. Therefore, they normally use transducers with a large number of piezoelectric elements (usually 128 or more), and their data are received and processed simultaneously. The reception in parallel of this data stream requires a large amount of space and processing capacity that is incompatible with portable application.

Patent application WO2008146207, filed on Dec. 4, 2008, entitled "Wireless Ultrasound Probe with Heads-up Display" by Poland et al, describes a wireless probe that pre-processes ultrasound data using a DSP (Digital Signalling Processor) embedded in a FPGA and sends it to an external host that performs final processing stages and transmits it to a display device, where the image has a low frame rate because of the limited bandwidth for image transmission.

US Patent Publication US2005/228281, filed on Oct. 13, 2005, entitled "Handheld diagnostic ultrasound system with head mounted display" by Nefos et al, describes a device that uses a dual core processor for the processing and management of images, with a limited resolution of 320× 240 pixels, visualization in a head mounted display connected by cable, and lacking the capacity for sending images to other devices in real time and at a high frame rate. Additionally, it does not provide for the emission of ultrasound waves.

U.S. Pat. No. 6,383,139, filed on May 7, 2002, entitled "Ultrasonic signal processor for power Doppler imaging in a hand held ultrasonic diagnostic instrument" by Hwang, describes an integrated architecture with display of information on a 5 inch screen that uses application-specific integrated circuits (ASIC) for all internal processes The device is portable but its size does not allow it to be handheld, such that it must be supported or located on a piece of furniture.

In general, no handheld portable ultrasound devices have been found that allow broadcasting of real time images at a high frame rate and using, for signal processing and device control, only a FPGA (Field Programmable Gate Array) platform without the need for other processors and a large RAM capacity.

SUMMARY OF THE INVENTION

One purpose of the invention is to have a handheld portable ultrasound device with control and processing centralized in its hardware with visualization outputs operating in real time, with high frame rate images. A description is thus provided for a device comprising
  a Power Supply,
  a Transducer comprising a plurality of piezoelectric elements emitting ultrasound waves and capturing echoes coming from tissues inside a patient;
  a FPGA (Field Programmable Gate array) Processing Unit comprising a General Device Control module,
  a Pulse Emission Control unit,
  a Beamforming module and
  an Image Processing module;
  a Pulse Generation and Front-End Unit comprising:
    a Pulse Generator,
    a plurality of transmission/reception switches and
    a Front-End circuit that generates a stream of digitized signal samples from echoes coming from tissues inside a patient;
  an Image and Transmission Unit that standardizes the image obtained by the Image Processing module and delivers it to a visualization medium; and
  a Visualization Device in which the General Device Control coordinates the operations of the Pulse Emission Control, Beamforming and Image Processing.

In operation, the Pulse Emission Control module activates the Pulse Generator; the Beamforming module receives the digitized signals or sample stream of the echoes coming from the tissues inside a patient from the Front-End circuit, applying selective delays to said digitized signals so as to provide a coherent summation of said digitized signals whereby the Image Processing module produces an image geometrically accurate of the tissues inside a patient by the coherent summation; and where the Pulses Generator supplies high voltage pulses to the Transducer. The plurality of switches of transmission/reception filter in amplitude the high voltage pulses. The Front-End circuit thus produces digitized signals from the echoes coming from tissues inside a patient.

In operation, the Image and Transmission Unit is connected wirelessly by an antenna to the Visualization Device which has an antenna and which comprises a wireless head mounted display. Alternatively, the Image and Transmission Unit may be connected to a Visualization Device through a cable.

The Power Supply is fed from a lithium ion polymer battery with a nominal voltage of 14.8V and is capable of delivering from 20 Vpp to 200 Vpp to the Pulses Generator for exciting the piezoelectric elements of the Transducer. The Pulse Generation and Front-End Unit uses a 16 piezoelectric element sliding window of the Transducer with a pulse up to 200 Vpp, where the pulse consists of one or more cycles of a square wave having a frequency that matches the resonance frequency of the piezoelectric elements. The FPGA Processing Unit is in charge of controlling the Pulses Generator and of processing the data captured by the Front-End to produce a B-mode ultrasound image, where the B-mode ultrasound image has 80 scan lines corresponding to the emission of pulses from each of the piezoelectric elements of the transducer. Each pulse emission is focused to a certain depth. In order to achieve a broad depth of field, each exploration line comprises two consecutive emissions of pulse in front of the same piezoelectric element, although with different focus, where the depth of both focuses is configurable. Also, the Pulse Emission Control activates the Pulse Generator with a determined phase shift pattern such that a wave front concentrates on a predetermined point. A single activation bit is required to start the shooting sequence of the 16 piezoelectric elements of the sliding window configured to focus an ultrasound beam to a depth at a predetermined point, where the application of the phase shifts is done by taking, as reference, the piezoelectric element nearest to the predetermined point to be focused. The referenced piezoelectric element always emits after a constant time interval after the moment when the activation bit initiating the shooting sequence is activated. This synchronizes the processing of the received signals, regardless of the predetermined point that was selected.

The Pulse Emission Control comprises a plurality of unitary pulsers, each one generating autonomously an ultrasound wave in a single piezoelectric element from a high-speed clock, whose frequency is higher than the resonance frequency of the piezoelectric elements of the Transducer. A unitary pulser is used for each piezoelectric element of the sliding window, enabling the application of a phase shift pattern with an accuracy equal to a period of the high-speed clock that the unitary pulser uses to produce the ultrasound waves.

For the application of the selective phase shifts, the data received from each piezoelectric element are oversampled by a process involving a FIR (Finite Impulse Response) low-pass digital filter where only non-null multiplications of the FIR filters are performed, thus reducing the use of multipliers and adders.

Finally, in order to generate an ultrasound image, the Image Processing module applies an envelope detection and a logarithmic compression to the sampling stream coherent summation, obtaining a scan line followed by another repeatedly, where each sample of each scan line is 8 bits wide and is stored on a RAM of 32 bit word width, allowing the storage of four samples at each address which is selected in such a way that for any memory address, the four samples correspond to two successive samples of two contiguous scan lines. This allows the system to obtain the value of each pixel with only one memory reading.

DETAILED DESCRIPTION OF PREFERRED EMBODIMENTS

This invention relates to a portable ultrasound device with control and processing centralized in the hardware and with visualization output in a wireless head mounted display.

In order to understand the functional blocks that make possible the generation of ultrasound images, it is necessary to briefly describe first the physical process and the logic behind the use of ultrasound to explore tissues inside a patient. This process consists of the emission of an ultrasound wave and the reception of its echoes. The simplest case is a single emitter and receiver which will only be able to obtain information from the tissues inside a patient right in front of it, forming a scan line. This form of operation is called A-mode.

Figure 1A:
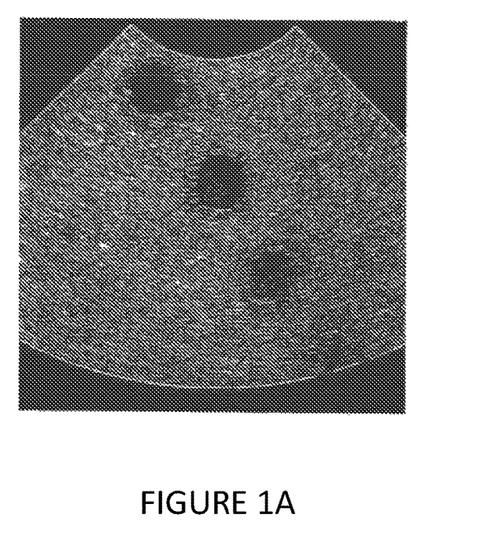
FIGS. 1A and 1B show a calibration pattern and the transducer that captures the image.
Figure 1B:
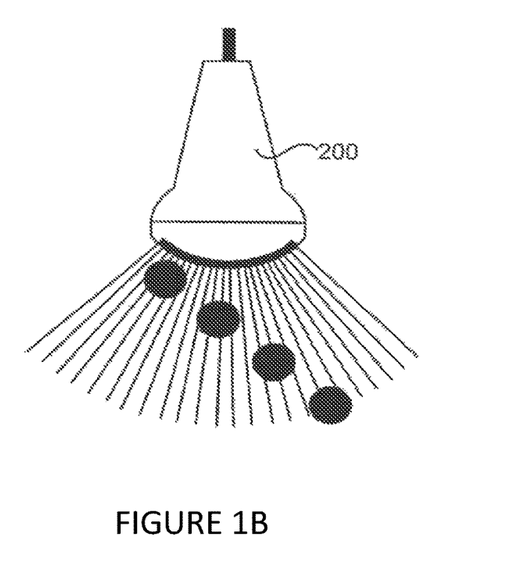

B-mode consists of the union of multiple scan lines in an organized way to form a bi-dimensional image. FIG. 1A shows an image in B-mode of a calibration pattern. FIG. 1B shows a diagram of a physical setup of the transducer that performed the ultrasound shown in FIG. 1A. The transducer of FIG. 1B, like most of the ultrasound transducers, is comprised by a linear array of piezoelectric elements capable of emitting ultrasound waves and capturing their echoes, organized in a convex shape which is the most common for general examinations.

The construction of the image starts with the emission of an ultrasound pulse in one direction and the capture of the echoes by multiple piezoelectric elements of the transducer. These echoes are digitized and coherently added to reinforce their intensities and to form a scan line, in which the power of the echo represents the brightness level in the resulting image. This process is repeated, each time changing the ultrasound waves emitting elements and also modifying the way in which the waves are added to focus towards different angles.

The union of all the exploration lines finally forms an ultrasound image in B-mode, which is the operation mode used in the handheld ultrasound device of this invention.

The digital processing of data in ultrasound applications is characterized by imposing high bandwidth and data processing rates, which implies that using traditional processing schemes, the amount of electronic resources drastically increases.

The main characteristic of the portable ultrasound device described below is that every logic control and all data processing is done in an FPGA (Field Programmable Gate Array) platform. An FPGA is a semiconductor device formed by logic elements that are blocks of basic digital electronics. Using a Hardware Description Language (HDL) it is possible to physically interconnect these blocks at will in order to provide the desired functionality.

One important objective is that the result of the development in FPGA provides hardware, not software. This is a relevant to differentiating this equipment from other pre-existing ones because, although FPGAs are previously used in handling ultrasound signals, traditionally there always were operations on signals performed by traditional processors using a combination of hardware and software to execute these tasks.

The main advantage of using this type of programmable electronics is the capability of generating logic blocks dedicated to specific operations.

A traditional processor has a predefined logic-arithmetic unit with a limited and pre-established number of adders and multipliers. When this amount is less than the amount required in each iteration, operations have to be done in multiple operation cycles that limit the processing times available. In many cases this is not compatible with processing equipment operating in real time unless there exists several traditional processors operating in parallel with the consequent increase of the space used and the cost of the electronics. Or, if a high-performance processor is available with a high operation frequency, higher cost, higher energy consumption and consequently higher heat generation result.

Using an FPGA it is possible to establish directly the number of multipliers and adders that will be available, with the possibility of optimizing the hardware to the specific application that is being developed. Thus, there will be as many adders and multipliers in parallel as necessary for the specific application with the sole limitation of the amount of logics and memory the FPGA offers to be configured.

Since one of the objectives of this development is the low cost, low range FPGAs are used which offer limited resources, but the freedom of being configured at will. This, combined with the intelligent use of these resources translates into a process that is computational, energetic and cost efficient.

Figure 2:
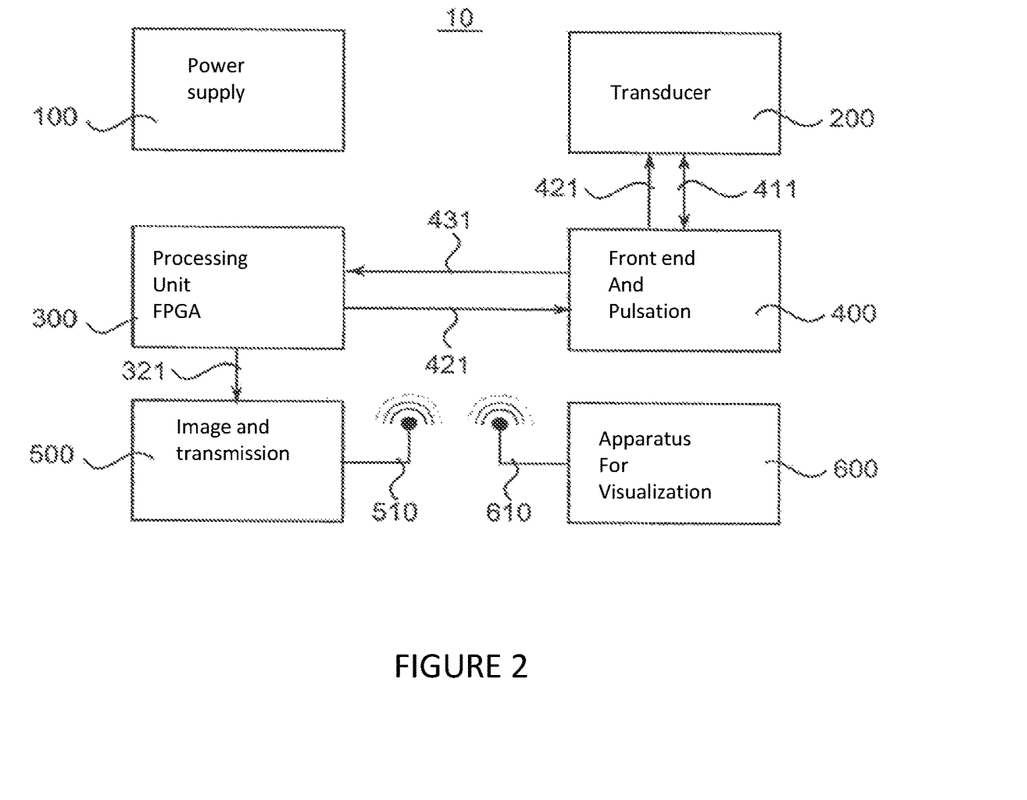
FIG. 2 shows the invention device comprised by its general functional blocks.

Considering the requirements of size, energy efficiency and integration level offered by available electronic components, a device comprised by the functional blocks shown in FIG. 2 is defined.

The handheld portable ultrasound device (10) is comprised by a Power Supply (100), a Pulse Generation and Front-End Unit (400), a Transducer (200) connected bi-directionally with the Pulse Generation and Front-End Unit (400); an FPGA Processing Unit (300) connected to the Pulse Generation and Front-End Unit (400) and also with the Image and Transmission Unit (500), where this Image and Transmission Unit (500) is connected wirelessly by its antenna (510) to a Visualization Device (600) that has an antenna (610).

The Transducer (200) has the function of emitting an ultrasound wave front. These ultrasound waves reflect from the tissues inside a patient generating echoes that are received and processed to produce an image from the inside of the body of the patient examined that are handled by the handheld portable ultrasound device (10). The Transducer (200) consists of a linear array of a plurality of piezoelectric elements (210) that can convert high voltage electric pulses into mechanical waves that spread through the tissues inside a patient and, when reflected by said tissues inside a patient, these waves produce echoes that are received by said piezoelectric elements (210) that transform the mechanic echoes into analog electrical signals that the Pulse Generation and Front-End Unit (400) digitize, while the FPGA Processing Unit (300) processes them to produce the image.

The Transducer (200) can be adapted to be used with any type of transducer available in the market oriented to portable equipment. For this particular embodiment, a standard transducer of the convex type C1-9/60R of 3.5 MHz from Contec® with 80 piezoelectric elements (210) is used.

In general, traditional ultrasound machines do not have major space, energy or processing capacity restrictions. Therefore they usually use a transducers with a large number of piezoelectric elements (usually 128 or more) which allow information to be received and processed simultaneously. Therefore, the reception in parallel of this data stream requires a large amount of space and processing capacity that are not compatible with a portable application. For this reason, in a portable ultrasound application, a multiplexing strategy is commonly used, limiting the number of elements that are effectively used simultaneously. Although an amount of information is sacrificed for the sake of reducing the electronics, multiplexing allows the dynamic selection of a limited set of the piezoelectric elements that provide the most relevant information on the area of interest.

In this particular embodiment, the C1-9/60R transducer used has a built-in multiplexer 80×16 (220), i.e. circuits that control the 80 piezoelectric elements (210) available, that allow the use of a moving window of 16 adjacent elements simultaneously. From now on, the name channel will be used to denote the electric medium through which the signals coming from each one of the 16 piezoelectric elements available in a given multiplexing state. It should be pointed out that the physical order of the piezoelectric elements (210) comprising the moving window has no fixed correspondence with the order of the channels through which the signals are transmitted. As a result, it is necessary that the handheld portable ultrasound device (10) make necessary adjustments to maintain the consistency of the signals.

The Power Supply (100) has the objective of providing power to the circuits that comprise the handheld portable ultrasound device. The power is delivered by a battery and should be managed as efficiently as possible to maximize the autonomy of the handheld portable ultrasound device (10). Since the emission, reception and processing of ultrasound waves require high energy consumption, it is indispensable to use high energy density batteries of reduced weight to improve the portability of the handheld portable ultrasound device (10). In this particular embodiment, lithium ion polymer batteries comprised of four 2000 mAh cells are used, connected in series, reaching a nominal 14.8V voltage. With these batteries, it is possible to provide energy for a period of up to two hours of continuous operation of the handheld portable ultrasound device (10). The energy control circuits are mostly comprised of switching regulators, available in the market and whose function is to generate the required voltage by the different functional circuits of the handheld portable ultrasound device (10) with the highest possible energy efficiency. In addition to the regulators that operate when the handheld portable ultrasound device (10) is on, this Power Supply (100) has specific integrated circuits to charge the battery, its monitoring and protection. The basic energy control functions, like monitoring the status of the battery charge sending power to the different regulators of the equipment, are done by a small micro controller of ultra low consumption to minimize the battery discharge in standy-by mode.

Figure 4:
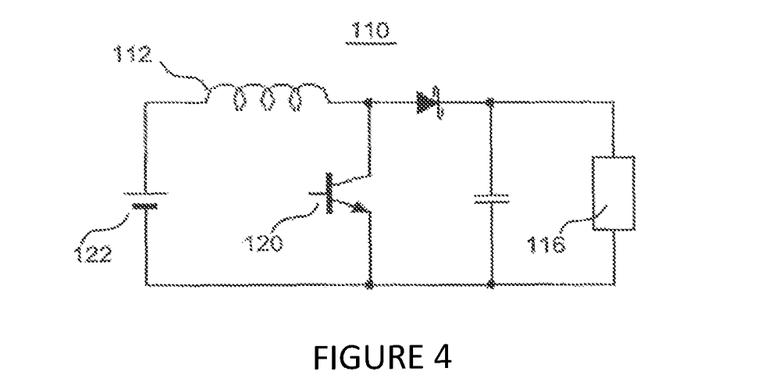
FIG. 4 shows an operational scheme of a commuted source of the Power Supply.

The emission of ultrasound waves towards the tissues inside a patient is produced by exciting the piezoelectric elements (210) of the Transducer (200) with high voltages relative to the ones that can be obtained directly from the batteries. Said voltages must be generated in the handheld portable ultrasound device (10) by a small size power supply, robust and reliable, efficient with a high energy capacity, with protections to avoid failures that may compromise the operation of the handheld portable ultrasound device (10) or the safety of the user. Given that the requirements described are specific, a voltage booster circuit (110) was designed to deliver up to 100V positive and negative, from the voltage of the 14.8V batteries, with a high energy efficiency as shown in FIG. 4; the voltage booster circuit (110) uses a standard configuration of the step-up type; additionally the voltage booster circuit (110) has current sensors—not shown—that measure the instant current in the inductance (112) and the average voltage in the output (116) to close the control loop. There are two voltage booster circuits (110): one for the negative and another one for the positive voltage.

The switching of the transistor (120) is managed by a micro controller—not shown—designed for controlling switching power supplies. The control program executed by the micro controller supervises the output voltage (116) and uses pulse width modulation to perform a control action and reach the voltage level given by a reference that is modifiable. Due to the above, the booster circuit (110) can generate configurable voltage levels between 14.8V and 100V on the positive side, whereas at the negative side, the range of voltage levels is 0V to −100V. Pulse firing transistors (120) of both voltage booster circuits (110) having the same frequency, in this case 25 kHz have been used, but can be changed according to design parameters and are offset by 180° to duplicate the apparent switching frequency of the voltage booster circuit (110) allowing the use of smaller filters to stabilize the input voltage (122).

The control program also incorporates the following security measures:

Main switch: The microcontroller can cut the energy of a voltage booster circuit (110) if any sign of malfunction is detected;

Limiting the duty cycle: To prevent catastrophic failures in the electronic components, the duty cycle of the switches is limited to a maximum level by preventing having the transistor (120) on continuously;

Overvoltage control: If the measured output voltage (116) exceeds 110 V positive or negative (any of them, independently), the switching semiconductors are stopped in the next operation cycle of the power supply (100). So, voltages are maintained within acceptable ranges for electronic components.

Overcurrent control: If a current exceeding a certain configurable threshold input is detected, the switching semiconductors in the next cycle are stopped immediately. This measure protects the power supply (100) from overloads.

Security measures described above, allow the power supply (100) to operate in a reliable way avoiding failures and even preventing component damage by failures in other components of the handheld portable ultrasound device (10). The power supply (100) implemented can deliver up to 10 W to the load continuously, with an efficiency of around 80%.

Figure 3:
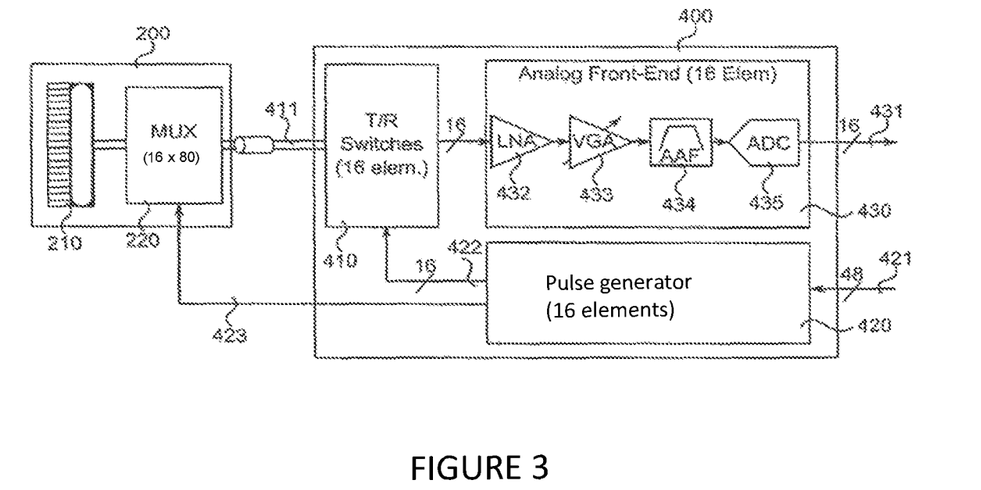
FIG. 3 shows in detail the Pulse and Front-End unit together with the transducer.

The Pulse Generation and Front-End Unit (400) described in FIG. 3 is intended to generate ultrasonic pulses that are sent to tissues within a patient and to capture echoes to form an image at the Visualization Device (600) from them.

The ultrasonic wave emission is done by exciting one or more piezoelectric elements (210) of the transducer (200) with a pulse whose voltage can reach 200 Vpp. Said pulse consists of a few cycles of a square wave whose frequency coincides with the resonant frequency of the piezoelectric elements (210). For this particular embodiment, the pulse consists of one cycle of a 3.5 MHz wave and by a moving window up to 16 elements can be excited simultaneously.

In order to produce this wave of large amplitude, high voltage switches commercially available are used. For example, the integrated MAX4940 has a maximum operating voltage of 220 Vpp and it incorporates four switches in a single package.

Given the capacitive nature of the piezoelectric elements (210) when exposed to high voltages such as those used to excite them, charge is accumulated on them, and it must be removed before it can properly receive the echoes. This results in a residual voltage, which should be brought to zero as soon as the pulse emission is completed. This is known as a clamping signal.

Figure 5:
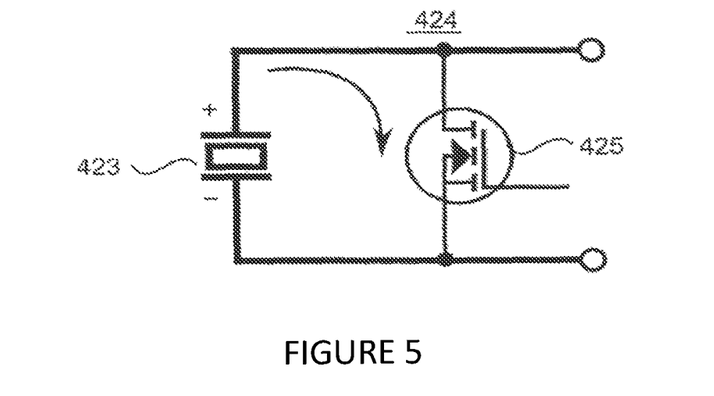
FIG. 5 shows an operational scheme on how to eliminate the remaining charge of a piezoelectric element.

FIG. 5 shows an active clamping circuit (424), which consists of a transistor (425) operating as a switch and is actuated right at the end of the active phase of emission of the pulse, allowing it to evacuate the remaining charge in the piezoelectric material (423) more effectively than a passive alternative, by providing a much lower resistance conduction. Once the remaining charge has been completely removed, the transistor (425) returns to the non-conducting state, preventing degradation of the received echoes from tissues within a patient. This mode of operation requires greater complexity in the circuit and the pulse emission control, but minimizes excessive power dissipation during active phases, improves energy efficiency and reduces the end use of semiconductors, both important aspects of the handheld portable ultrasound device (10). In the embodiment, the integrated circuit MAX4940 included in the pulse generator (420), incorporates clamping transistors and the control of the pulse emissions is carried out by the processing unit FPGA (300) through digital lines (421).

A first step in receiving the ultrasonic echoes is a transmit/receive commutator (410). Its purpose is to provide a high impedance to high voltages, but a low impedance to low voltages, i.e., to prevent the high voltages of the pulses that excite the piezoelectric elements (210) passing through towards the Front-End circuits (430), but allowing the weak echoes to pass for their capture and processing.

In the embodiment, a solution provided by the integrated MAX4936, of MAXIM®, circuit is used. This integrated circuit includes 8 transmission/reception switches able to support voltages up to 220 Vpp in the high voltage side, while limiting the output signals to 1 Vpp in the low voltage side. The high voltage pulses emitted by the Pulse Generator (420) are directed towards the electrical channels (411) through transmission/reception switches (410) via electrical connections (422), which are driven by the integrated circuit MAX4936 into the high voltage side in a safe way.

The Front-End circuit (430) is designed to capture the electrical signals corresponding to echoes from the piezoelectric elements (210), and digitizing them for their processing. It is divided into 4 stages through which the analog signal must pass and these steps are integrated for the preferred embodiment, in a single device manufactured by Analog Devices® Company, whose part number is AD9272.

In the first step LNA (432), the electrical signals representing ultrasonic echoes from tissues within a patient are amplified by a specific low noise amplifier.

Ultrasonic waves lose intensity in an exponential way as the depth of penetration increases into the patient's tissue. Said decay is reflected in the intensity of the electrical signals captured by the handheld portable ultrasound device (10), which reduces their intensity as time goes on, since the deepest echoes take longer to arrive at the transducer (200). To compensate for this phenomenon, the Front-End (430) incorporates a Time Gain Compensation or TGC. This stage comprises a variable gain amplifier (433) controlled in real time by the Processing Unit FPGA (300).

Prior to the digitization of the data it is necessary to apply, to the compensated signal a filter (434) whose purpose is to prevent aliasing by eliminating frequency components higher than half of the sampling frequency. This filter is incorporated into the AD9272 and is configurable to be useful to increase or decrease the bandwidth of the signal that will be digitized. Finally, an analog to digital converter ADC (435), converts the echoes into a bit stream and delivers them to the processing unit FPGA (300) by a link (431). The ADC (435) takes samples at a rate of 10 MSPS allowing it to represent the information in the band around 3.5 Mhz.

Figure 6:
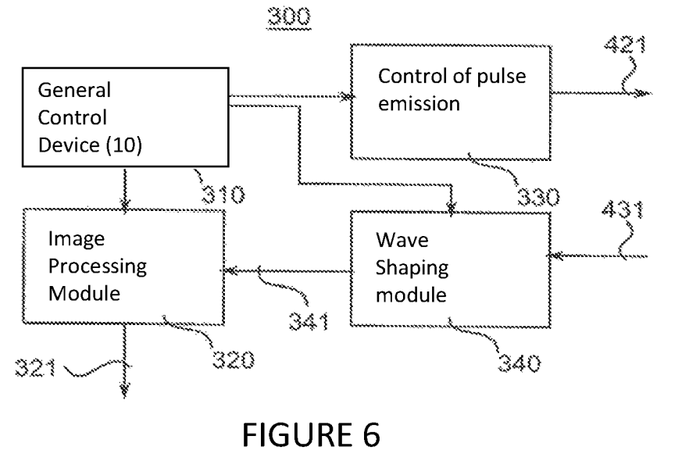
FIG. 6 shows in detail the FPGA processing unit.

The FPGA processing unit (300) is responsible for controlling the pulse generator (420) and processing the data captured by the Front-End (430) to generate a B-mode ultrasound image. A B-mode ultrasound image consists of a series of scan lines.

In the present invention, an image has 80 scan lines corresponding to the pulse emission for each of the piezoelectric elements (210) of the transducer (200). Each pulse emission can be performed focusing on a certain depth, and to achieve a wide focal range; each scan line comprises two consecutive pulses centered to face the same piezoelectric element (210), but with a different focus, where the depth of the two foci is configurable.

The General Device Control Unit (310) is in charge of communicating to the Pulse Emission Control Unit (330) when and how to generate the ultrasonic waves, besides keeping track of the number of samples received and the scanning lines performed. Along with this, sync signals are generated for the rest of the Processing Unit FPGA (300), indicating when it is taking samples, when a scanning line is completed and when an image is completed.

Figure 7:
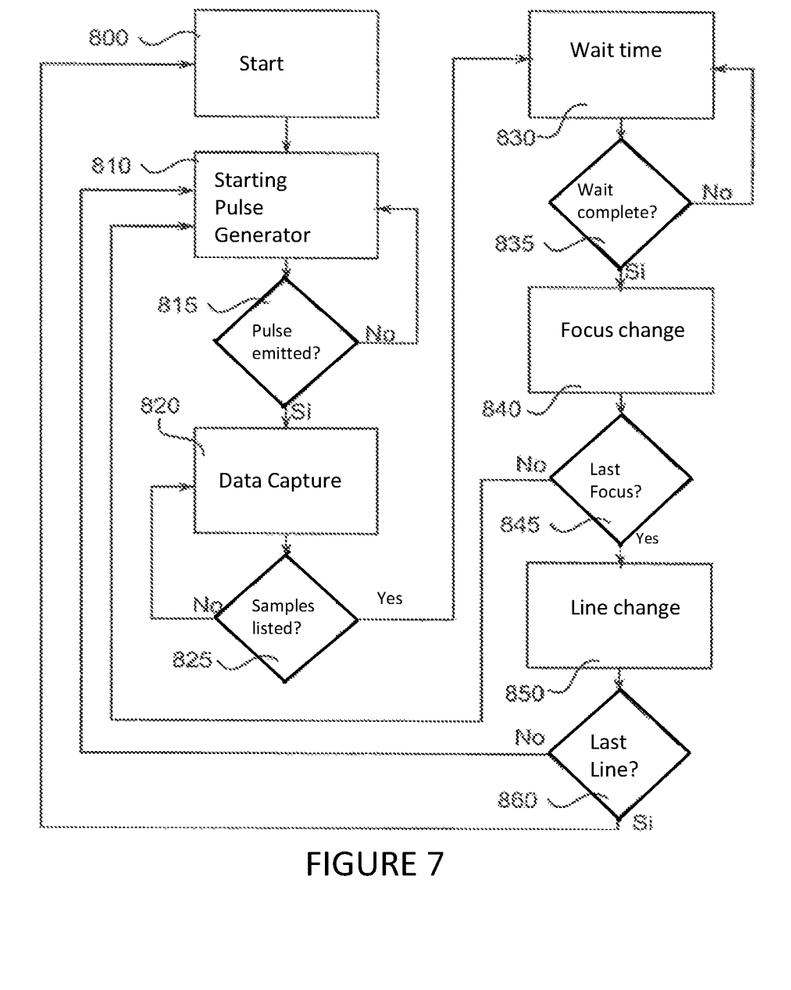
FIG. 7 shows a flow diagram for pulse emission control.

This process is described in FIG. 7, and the steps are listed below:

Start (800): all counters are reset to zero;

Starting of Pulse Generator (810): the scan line and selected focus for the emission used to initiate data capture are determined. A flag is received from the Pulse Emission Control Unit (330) that indicates that a pulse emission has been made (815) to activate the signal that indicates to the rest of the FPGA Processing Unit (300) that a data capture will begin.

Data Capture (820): upon receiving the signal to start capturing data, data is received from the Front-End (430), which are processed by a Beamforming module (340); whenever the Beamforming module (340) generates a new sample for the Image Processing Module (320) a counter is increased and the Image Processing module (320) is instructed to store it in a memory, which is not shown, and continued until it reaches the number of samples required (825) for the current focus.

Dead Time (830): before changing focus or scan line and a new emission of ultrasound pulses, there is a configurable Waiting Time (835) to ensure that there are no remaining echoes that may affect the following data capture (820); this time can be adjusted to increase or decrease the frame rate of the generated image.

Focus change (840) to obtain an image composed by two foci, each scan line is captured twice. First, 2000 samples with the deepest focus are captured, then the focus is changed to the closest one and returned to the initial state of the pulse generator (810) to pulse again, capturing fewer samples, depending on the depth of the second focus; once it has completed the scan line, it moves to the next scan line (845); changes scan line (850), upon reaching this state the count of scan lines is incremented by one and a sync signal of scan line change is generated; if the 80 scan lines are not completed (860) it returns to the starting stage of the Pulse Generator (810), or otherwise, an image sync signal is emitted and it returns to the Home (800) state to start the following scan line.

Unless the button is pressed to freeze the image, this process is not stopped, getting a frame rate of about 35 frames per second.

The high frequency pulses that finally excite the piezoelectric elements (210) of the transducer (200) are generated in the Pulse Generator (420), which is controlled from the FPGA Processing Unit (300) by the Emission Control Pulse (330) connected by digital lines (421).

The fundamental Pulse Emission Control Unit (330) is a unitary pulser, not shown, whose purpose is to generate the sequence of on and off signals of transistors comprising the pulse generating circuit for a single piezoelectric element.

The unitary pulser is programmed to generate a cycle of 3.5 MHz, along with the clamping signal. Its only input bit starts the whole sequence. An independent unitary pulser is used for each of the electrical channels (411), each of which is directed to a piezoelectric element (210) within the moving window through multiplexing circuits (220).

The unitary pulser operates with a 140 MHz clock, that is 40 times the frequency of the pulses generated. As the pulse sequence begins at the 140 MHz clock edge following the activation moment of the starting signal, the ability to apply relative phase shifts between the pulses of different channels with a resolution of 9° is obtained.

Figure 8:
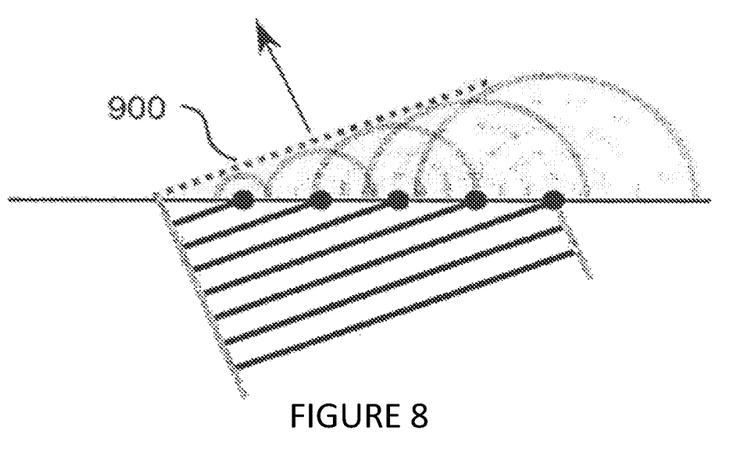
FIG. 8 shows the behaviour of a waves front.

According to Huygens' principle, every point of a wavefront can be considered as a spherical wave source (900) of equal speed and frequency as the original front, as shown in FIG. 8.

Conversely, since a piezoelectric element (210) of the transducer (200) can be considered as a point source of spherical waves (900) given its small size, to emit ultrasonic pulses with multiple piezoelectric elements (210), it generates a wavefront (900) whose shape can be manipulated by applying controlled phase shifts to the pulse signals.

Figure 9:
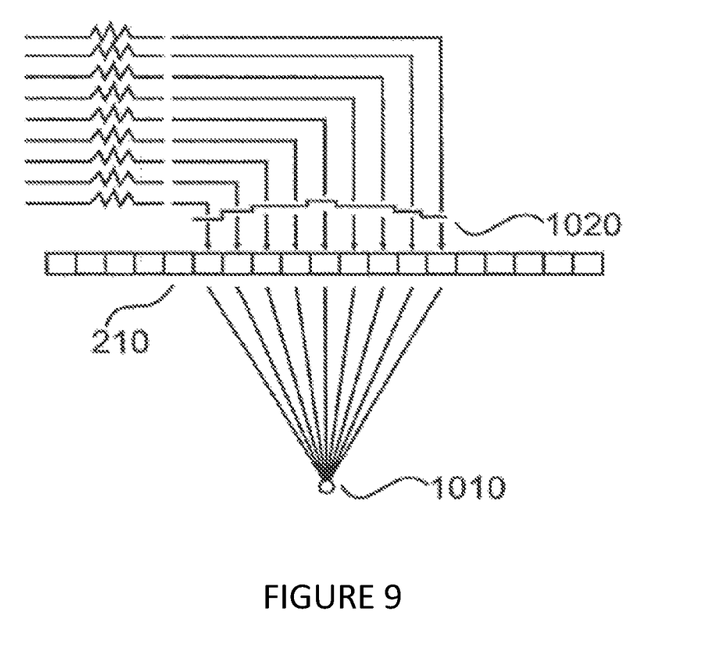
FIG. 9 shows the phase shift pattern of the pulses.

Emission Control Pulse (330) establishes a phase shift pattern (1020), such that the wavefront (900) is focused to a predetermined point (1010) of space, in order to increase the resolution in that area and signal power received by pulsing with multiple piezoelectric elements (210), as seen in FIG. 9. It also allows focusing the beams to several predetermined points (1010), whose associated phase shifts (1020) have been previously calculated offline. These points are directly in front of the center of the moving window of 16 active piezoelectric elements (210), given a certain multiplexing at different depths.

The Emission Control Pulse (330) drives the Pulse Generator (420) with the corresponding phase shifts (1020), so it requires a single bit of activation to initiate the pulse sequence of the 16 piezoelectric elements (210) configured to focus the ultrasound beam at a depth at a predetermined point (1010).

The phase shifts (1020) are referenced to the piezoelectric element (210) closest to the predetermined point to focus (1010). Since this element is the last to pulse, its waves arrives at the focus point (1010) at the same time as those from the other piezoelectric elements (210) that are at a greater distance. The reference piezoelectric element (210) always emits after a constant time interval from the instant the activation bit initiates the pulsing sequence.

This feature is essential to synchronize the processing of the received signals, regardless the selected predetermined point (1010).

The complete sequence for generating an ultrasonic wave front focused at a predetermined point (1010), involves selecting the moving window of 16 piezoelectric elements (210) to be used to capture the data. In addition, the Pulse Emission Control (330) is responsible for sending instructions to the Multiplexing Circuitry (220) incorporated in the Transducer (200) via a connection (423) to select the desired piezoelectric elements (210); it is possible to select 64 different moving windows of adjacent piezoelectric elements (210) in the Transducer (200). Emission Control Pulses (330) is also responsible for properly directing the pulses generated by the corresponding piezoelectric elements (210), since the electrical channels in the electrical circuitry (411) have no fixed correspondence with physical channels of the different possible moving windows.

The following describes in detail the signal beamforming process employed in the handheld portable ultrasound device (10).

Figure 10:
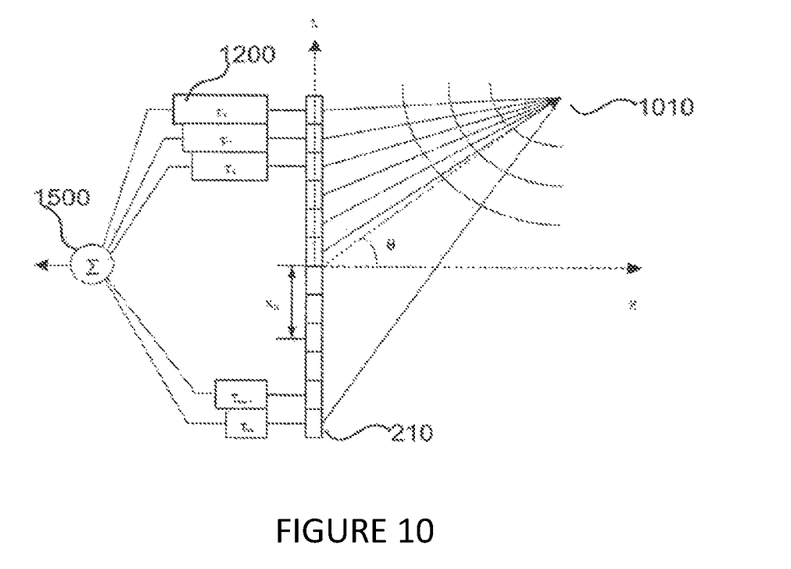
FIG. 10 shows the compensation delays in the piezoelectric elements.

The signals received from the Transducer (200) correspond to the echoes from tissues within a patient. As seen in FIG. 10, echoes travel different distances from a predetermined point (1010) of interest, particularly to each of the piezoelectric elements (210) of the Transducer (200), so that the arrival of ultrasonic waves occur at different times. Therefore, to extract from this set of signals the corresponding information from this predetermined point (1010) of interest, it is necessary to compensate this physical phenomenon by applying selective delays (1200) to the data received from each piezoelectric element (210). The resulting signals are summed to generate a single signal that consistently contains coherent information of interest, called coherent summation (1500). The introduction of selective delays (1200) and the coherent summation (1500) are illustrated on the left side of FIG. 10; this process is called beamforming.

In practice, this process is implemented in digital systems that have a certain sampling rate $f_s$. Analog signals are digitized using an A/D circuit, obtaining a sequence of discrete values $x_s$, representing the original signal. For this representation to be valid and no information be lost in the digitization process, it is required that the sample rate $f_s$ meets the Nyquist criterion.

In this particular embodiment, the AD Converter (435) of the Front-End (430) captures data at 10 MSPS, i.e., one sample every 100 ns. However, for the selective delays (1200) to allow to extract information accurately from the predetermined point (1010) of interest, it is necessary to have a temporal resolution of at least 40 MHz, steps of 25 ns.

As in any electronic device, when higher the sampling rate, the higher the overall energy consumption of the system, mainly due to switching losses. Energy limitations imposed by the requirement of portability, prevent carrying out a sampling at sufficiently high rates to apply directly the precise delays at each received signal.

To resolve this situation, a commonly used strategy is to digitally increase the sampling rate times through an interpolation process of a determined order O. This interpolation is performed by a process called zero padding, in which (1–1) zeros are introduced between each sampled data $x_s$ to obtain a sequence $\tilde{x}$. Then to the sequence $\tilde{x}$ a low pass FIR filter $h_{lp}$ is applied, obtaining an oversampled data set.

Through this oversampling, the needed samples apply delays with the adequate precision without increasing sampling rates are estimated. However, the traditional ways of doing this over sampling have the disadvantage of a high computational cost, in terms of processing and memory required, resulting in an increase in the size of the required electronics.

In this particular embodiment, the implementation of this interpolation is a development that cleverly exploits the nature of the process to significantly reduce its computational cost, allowing its application in portable devices or others that have limitations on its processing power. The implemented interpolation predicts when the results of multiplication are null, preventing them from performing unnecessarily, resulting in savings in the processing computational costs. It uses a filter $h_{lp}$ FIR of order O, consisting of (O+1) coefficients $a_n$ with n=1 . . . (O+1) properly designed. Normally the application of this filter corresponds to an input-output relationship of the form:

$$y_k = \sum_{i=1}^{O+1} a_i \tilde{x}_i(k)$$

However, it is known that the input data to this filter have the following feature:

$$\tilde{x} = \begin{cases} x_s; & k = c*l \\ 0; & \sim \end{cases}$$

Then, noticing that in each iteration just one of each l multiplications is not null, proper multiplexing logic may be used to select the non-zero pairs $a_i\tilde{x}_i(k)$, preventing null multiplications, reducing the necessary electronics.

With this, the method developed reduces in l times the amount of adders and multipliers used to perform the operation. For example, if it is required to do an interpolation of order 39 to increase 4 times the sampling frequency, traditionally it will require 40 multipliers and 39 adders in order to perform the operation. With the above proposed solution, this number is reduced to 10 multipliers and 9 adders, which results in more efficient electronics from the point of view of calculation, the circuit size and use of the energy.

Selective delays (1200) are applied to the interpolated signals and finally they are coherently (1500) summed to generate a single stream of beam formed data (341).

The beam formed data (341) goes to the Image Processing Module (320), which performs envelope detection of the conformed data (341) and then a logarithmic compression over the samples in order to emphasize the weakest echoes. The resulting data are 8-bit numbers corresponding to the brightness levels of each display scan line sample.

Finally, the image processing module (320) generates a bi-dimensional image, consistent with the geometry of the tissues inside the patient being examined. This process is important when the Transducer (200) has a convex shape, since the scan lines represent brightness levels in polar coordinates and should be displayed on a screen in Cartesian coordinates.

Figure 11:
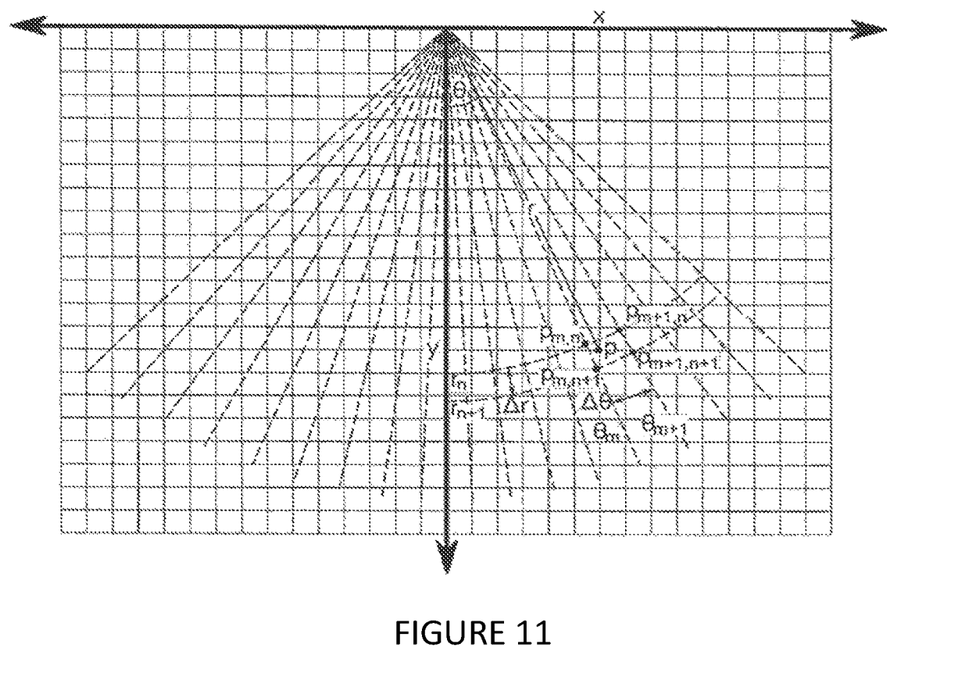
FIG. 11 shows a bi-lineal interpolation scheme.

The handheld portable ultrasound device (10) generates images in VGA format, i.e., with resolution of 640×480 pixels. This requires a fully developed FPGA implementation of a bilinear interpolation, where the processing of each pixel is made in synchronization with the scanning of the screen on order to permit a frame rate of 60 frames per second, and eliminating the need to use a high-speed memory to store the screen image. With this, it is not necessary to include a processor, as it is done in most computers, which avoids the use of high frequency clocks and reduces the energy consumption. For the transformation from polar coordinates to Cartesians coordinates, each pair (x,y) of a pixel on the screen is translated to polar coordinates in space, to which belong the scan lines, depending on the zoom level and image position set by the user.

In sync with the scanning of the screen, to each pixel is assigned a radius r and an angle θ in the following way:

$$r = \sqrt{x^2 + y^2}$$
$$\theta = \mathrm{atan}\left(\frac{x}{y}\right)$$

Since the FPGA has only addition and multiplication operations, it should generate dedicated modules to solve these calculations. The square root is a widely known problem, so that a module provided by the manufacturer of the integrated circuit is used. For the arc tangent function, implementations are not available to allow a result in one clock cycle, so a Look Up Table (LUT) that receives the result of x/y and delivers the θ value has been implemented. As the amount of the FPGA logic elements is reduced, considering is the asymptotic nature of the function, the LUT is divided into two parts; a finer part for angles less than 85° and a coarser part for the rest. With this, an acceptable accuracy is obtained for the angle valid for the entire space of interest, without generating too large a table.

From samples of the scan lines closer to the pair (r, θ), called $p_{m,n}$; $p_{m+1,n}$; $p_{m+1,n+1}$ and $p_{m,n+1}$, shown in FIG. 11, the brightness level corresponding to the pixel (x,y) is calculated interpolating in the following way:

$$p = \frac{(\theta - \theta_m)(r - r_n)p_{m+1,n+1} + (\theta - \theta_m)(r_{n+1} - r)p_{m+1,n} + (\theta_{m+1} - \theta)(r - r_n)p_{m,n+1} + (\theta_{m+1} - \theta)(r_{n+1} - r)p_{m,n}}{\Delta r \cdot \Delta \theta}$$

Samples of a scan line, arrived as 8 bit numbers corresponding to a brightness level on the screen, are stored in a SRAM memory as a 32 bits word, allowing four samples to be stored in each address, which are selected so that for any memory address, the 4 samples correspond to $p_{m,n}$; $p_{m+1,n}$; $p_{m+1,n+1}$ and $p_{m,n+1}$, for a given pair (r θ). Thus, to obtain the value of a pixel, the address is calculated in point memory $p_{m+1,n+1}$ and the 4 data required for interpolation are obtained, which is performed in only one memory reading instead of 4 to draw a pixel at screen, relaxing the requirements for memory speed, enabling the use of less expensive memories and lower energy consumption.

The invention is designed for use with one hand, so the management of the basic functions are performed through an on screen menu, which is operated with four directional buttons plus one to enter and exit the menu items. The functions that the user can access are:

Framing
Zoom
Gain
Focus
Brightness and Contrast

A parameter control module receives the signals of the five buttons and modifies the registers with the values of each function. While the number of menu items is fixed to the user, the design of the module allows adding more features later. The register values are given to the corresponding modules for the modified parameter.

Figure 12:
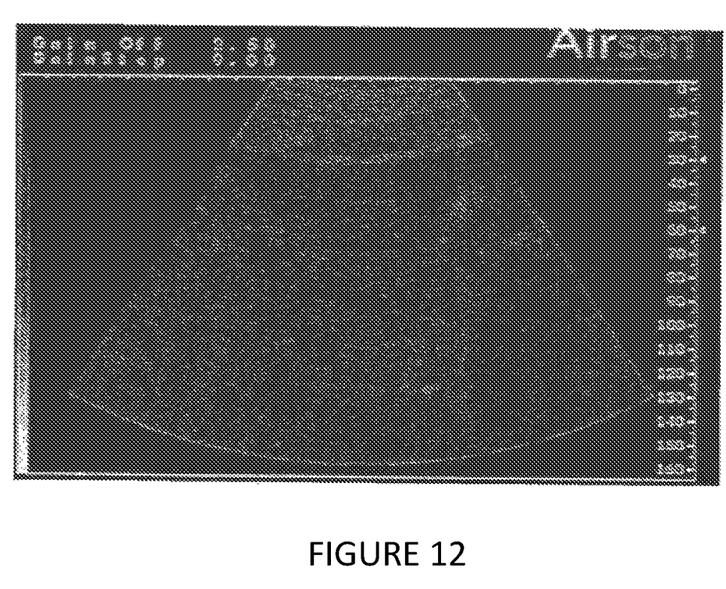
FIG. 12 shows a view of the graphic interface with the menu.

This module is also responsible for displaying the on screen menu, which contains a character generator, where the size of each character is 16×16 pixels, which can be drawn on a grid that covers the entire screen. The text is stored in a RAM memory with ASCII encoding, where each address corresponds to a cell of the screen. Each character is associated with a LUT that receives the position of the scanning of the screen and delivers the level of opacity between 0 and 15, corresponding to the pixel drawn. This level of opacity is merged with the image obtained after the processing to generate the graphical interface of the device, as shown in FIG. 12.

The Image Processing Module (320) is capable of saving captures of images generated in files stored in an SD memory card, according to the standard FAT format.

Finally, the output of the Image Processing Module (320) is a data stream (321) corresponding to an image of 640×480 pixels with a format consistent with the VGA standard.

The VGA standard consists on the analog transmission of a video signal to a display apparatus through three signals encoding, by voltage level, the intensity of red, green and blue colors for each pixel. The standard also has two synchronization signals indicating to the display apparatus when it ends one line and when it ends a frame.

To obtain the analog signals required by the VGA standard, the Imaging and Transmission Unit (500) converts the digital signals from the Image Processing Module (320) to analog signals.

The Imaging and Transmission Unit (500) also implements the necessary circuitry to convert the image in VGA format to NTSC format. The latter is widely used for video transmission for display devices such as televisions, projectors, etc.

Generating images in VGA format and its conversion to NTSC allow the handheld portable ultrasound device (10) to operate also in a stationary way, connected to a standard computer monitor by a cable. Thus the handheld portable ultrasound device (10) has two operation modes, one stationary and one portable and handheld.

For a portable and handheld operation with wireless transmission of images to the display device (600), the Imaging and Transmission Unit (500) has a commercially available analog transmitter, which modulates and transmits the NTSC signal in the 5.8 GHz band. The transmitted signal can be received by one or more analog receivers, also commercially available.

An alternative embodiment of the handheld portable ultrasound device (10) implements digital coding JPEG2000 instead of NTSC for transmitting images to the display apparatus (600). Said encoding is performed using specialized integrated circuits for this purpose and commercially available. The use of digital compression allows a more efficient use of the wireless transmission channel, thereby improving the image quality in the display apparatus (600) and greater robustness thereof to changes in reception quality, product of the incorporation of overheads with redundancy and error correction algorithms. For the transmission of these digital signals, Wi-Fi modules are used, which reach the transmission rates required for transmitting images in real time.

The display apparatus (600) is intended to show the ultrasound image generated by the handheld portable ultrasound device (10) in real time to the user. For the preferred embodiment, the Display Apparatus (600) receives radio frequency signals through an analog reception module, which demodulates and reproduces the NTSC signal generated by the Imaging and Transmission Unit (500). This signal is sent to the device that reproduces the image so that the user can see it.

In the preferred embodiment, head mounted displays are used, which have a control circuit of LCD screens that display the image (one for each eye), which can decode the signal in NTSC format. An analog reception module is mounted inside the case of the HMD, it also holds batteries and charging circuits making them totally wireless.

As the NTSC format is so common, it is possible to use the reception circuits to deliver the signal generated by the Imaging and Transmission Unit (500) to any compatible device, such as televisions, projectors, video capture devices, etc.

For the alternative embodiment with digital encoding, a Wi-Fi module receives digitized image data and compressed according to the JPEG2000 standard format. Decompression of the data is performed by a specialized integrated circuit, its output is decoded by dedicated circuits to directly handle the LCD screens displaying the image in the head mounted displays according to the standard.

The invention claimed is:

1. A handheld portable ultrasound device for delivering real time visualization of tissue inside a patient, comprising:
   a power supply (100);
   an ultrasonic transducer (200) comprising a plurality of piezoelectric elements (210);
   a Pulse Generation and Front-End unit (400) comprising:
      a Pulse Generator (420);
      a plurality of Transmission/Reception Switches (410);
      a Front-End circuit (430) for a plurality of analog channels; and
      a plurality of channels in parallel (431);
   an Image and Transmission Unit (500);
   a Visualization Device (600) for displaying at least 640× 480 resolution and 60 frames per second frame rate visualization outputs; and
   a FPGA (Field Programmable Gate Array) digital logic control and data processing unit in which logic blocks are implemented and interconnected in hardware alone and in which bilinear interpolation is performed in hardware alone, said FPGA comprising:
      a General Device Control Module (310);
      a Pulse Emission Control Module (330);
      a Beamforming Module (340); and
      an Image Processing Module (320).

2. The device according to claim 1, wherein the Image and Transmission Unit (500) is connected wirelessly through an antenna (510), to a Visualization Device (600) also having an antenna (610).

3. The device according to claim 1, wherein the Visualization Device (600) consists of a wireless head mounted display.

4. The device according to claim 1, wherein the Image and Transmission Unit (500) is connected to the Visualization Device (600) through a cable.

5. The device according to claim 1, wherein the Pulse Emission Control Module (330) is comprised of a plurality of independent pulser units for generating control signals for the Pulse Generator (420).

6. The device according to claim 1, wherein said FPGA is configured for performing bilinear interpolation absent use of memory to store a screen image.

7. A method to generate at least 640×480 resolution and 60 frames per second frame rate output images using a handheld portable ultrasound device, said device consisting of a digital FPGA (Field Programmable Gate Array) circuit performing logic control and data processing exclusively in hardware alone, said process comprising the steps of:
   delivering high voltage pulses with a phase shift pattern (1020) through a Pulse Generation (420) and a Front-End Unit (400) to a transducer (200);
   converting the high voltage pulses into ultrasonic waves through a plurality of piezoelectric elements (210) of the transducer (200);
   emitting a wave front (900) through said plurality of piezoelectric elements (210) of said transducer (200) in the direction of a patient's tissue;
   capturing echoes using a plurality of piezoelectric elements (210) of said transducer (200);
   digitizing said captured echoes through a Front-End (430) circuit so as to generate a stream of digitized signals;
   applying selective delays (1200) to the stream of digitized signals to formulate a coherent summation (1500) of the stream of digitized signals;
   normalizing the stream of digitized signals; and
   transforming the normalized stream of digitized signals into an image, using an Image and Transmission Unit (500) to display it on a Visualization Device (600);
   wherein the FPGA processor performs the following functions:
   coordinates operation of a General Device Control Module (310) the operation of: Pulse Emission Control Module (330); Beamforming Module (340); and Image Processing Module (320);
   actuates the Pulse Generator (420) through the Pulse Emission Control Module (330), to send high voltage pulses with a shift pattern (1020) to the transducer (200) of the first step, where said ultrasonic wave front (900) is focused in the predetermined point of interest (1010);
   receives in the Beamforming Module (340) said stream of digitized signals from the echoes; and
   generates a geometrically accurate image in the Image Processing Module (320) from the coherent summation (1500) of the stream of digitized signals.

8. The method according to claim 7, where in the first step the phase shift pattern of pulses (1020) is applied to said piezoelectric elements (210), focusing the ultrasonic wave front (900) to a predetermined point of interest (1010), calculated previously off-line.

9. The method according to claim 7, wherein in the step of applying selective delays the stream of digitized ultrasound signals received by the Beamforming Module (340), come from 16 digital channels in parallel (431) and from the Front-End (430), where the Beamforming Module (340) oversamples through a process with a low-pass FIR (Finite Impulse Response) filter, performing only non-null multiplications of the FIR filter.

10. The method according to claim 7, further comprising the steps of:
   performing envelope detection over a single stream of digitized signals; and
   logarithmically compressing the stream of beamformed samples (341) and storing the beamformed samples (341) in a memory, ordered in 32-bit words, each one containing 4 8-bit samples, corresponding to necessary samples to calculate the final brightness value of a pixel on screen, whose coordinates are within the area defined by the samples, allowing the calculation of each pixel from only one memory reading operation.

11. A Field Programmable Gate Array (FPGA) for use in a handheld portable ultrasound device, said FPGA configured to comprise in hardware:
   a General Device Control Unit (310),
   a Pulse Emission Control Unit (330),
   a Beamforming Module (340), and
   an Image Processing Module (320)
   wherein the General Device Control Unit (310) coordinates the operation of the Pulse Emission Control Unit (330), the Beamforming Module (340) and the Image Processing Module (320); the Pulse Emission Control Unit (330) drives a Pulse Generator (420); the Beamforming Module (340) receives a plurality of digitized signals streams from echoes applying selective delays (1200) to those digitized streams to deliver a coherent summation (1500) of said digitized streams and where the control of the FPGA operation is performed in hardware.

12. The FPGA of claim 11 configured to drive the Pulse Generator (420) and to process data captured by a Front End (430) of a handheld portable ultrasound device in order to generate an ultrasound image, where said image has approximately 80 scan lines corresponding to pulse emissions of said ultrasound device, wherein each pulse emission is configured to focus to a particular depth, and each scan line is comprised of two consecutive pulse emissions in front of a same piezoelectric element (210) but with a different focus.

13. The FPGA of claim 11 wherein the Pulse Emission Control Unit (330) is adapted to drive a Pulse Generator (420) with a phase shift pattern (1200) so that a wave front (900) is concentrated to a determined point (1010), requiring only one activation bit to start the whole pulsing sequence of piezoelectric elements (210) in a moving window configured to focus the ultrasonic beam to a depth at the determined point (1010), where the phase shifting (1020) is made taking the piezoelectric element (210) nearest to the determined point (1010) to focus as the reference, and where said reference piezoelectric element emits after a constant time interval from the moment when the activation bit initiates the pulsing sequence in order to synchronize the processing of the received signals regardless of the determined point (1010) selected.

14. The FPGA of claim 11 wherein the Pulse Emission Control Unit (330) comprises a plurality of unitary pulsers, each adapted to generate autonomously an ultrasound wave in a single piezoelectric element (210) generated from a clock, with frequency at least an order of magnitude higher than the resonant frequency of piezoelectric elements (210) of a Transducer (200), and where said clock determines the resolution of phase shift between channels.

15. The FPGA of claim 11 wherein, in order to apply said selective delays (1200), the FPGA causes data to be oversampled using a process that involves a low pass Finite Impulse Response digital filter in which only the non null multiplications are made.

16. The FPGA of claim 11 where, in order to generate an echography image, the Image Processing Module (320) applies envelope detection and logarithmic compression to the coherent summation (1500) of said at least one of digitized signals or sample stream, and obtains a scan line that occur continuously, wherein each sample of each scan line is 8 bits wide and is stored in RAM memory with a word width of 32 bits, thereby allowing for storage of four samples on each address, said address selected in such a way that for any memory address, the four samples correspond to two consecutive samples of two contiguous scan lines, so as to allow the calculation of each pixel with only one read operation.

17. The FPGA of claim 11 wherein said plurality is 16 digital signals or sample streams.

18. The FPGA of claim 11 wherein said coherent summation is performed as said signals or streams are being received.

19. The FPGA of claim 11, wherein said FPGA performs addition and multiplication mathematical absent use of a processor.

* * * * *